United States Patent
Stinson

(10) Patent No.: US 8,048,141 B2
(45) Date of Patent: Nov. 1, 2011

(54) MEDICAL DEVICE THAT SIGNALS LUMEN LOSS

(75) Inventor: Jonathan S. Stinson, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1326 days.

(21) Appl. No.: 11/006,018

(22) Filed: Dec. 7, 2004

(65) Prior Publication Data

US 2006/0122683 A1 Jun. 8, 2006

(51) Int. Cl.
*A61F 2/06* (2006.01)

(52) U.S. Cl. ........ 623/1.15; 116/203; 116/266; 116/272

(58) Field of Classification Search .................. 600/486, 600/481, 505, 553, 587; 604/890.1; 361/628
See application file for complete search history.

(56) References Cited

U.S. PATENT DOCUMENTS

| | | | |
|---|---|---|---|
| 4,881,034 A * | 11/1989 | Kaufman et al. ............. 324/318 | |
| 5,411,551 A | 5/1995 | Winston et al. | |
| 5,967,986 A | 10/1999 | Cimochowski et al. | |
| 6,053,873 A * | 4/2000 | Govari et al. .................. 600/505 | |
| 6,231,516 B1 * | 5/2001 | Keilman et al. ............... 600/485 | |
| 6,264,611 B1 * | 7/2001 | Ishikawa et al. .............. 600/486 | |
| 6,277,078 B1 * | 8/2001 | Porat et al. ..................... 600/486 | |
| 6,280,385 B1 * | 8/2001 | Melzer et al. .................. 600/423 | |
| 6,284,078 B1 * | 9/2001 | Witonsky et al. ................ 156/85 | |
| 6,308,715 B1 | 10/2001 | Weissman et al. | |
| 6,416,474 B1 | 7/2002 | Penner et al. | |
| 6,442,413 B1 | 8/2002 | Silver | |
| 6,475,170 B1 * | 11/2002 | Doron et al. .................... 600/587 |
| 6,486,588 B2 * | 11/2002 | Doron et al. .................... 310/322 |
| 6,504,286 B1 * | 1/2003 | Porat et al. ...................... 310/324 |
| 6,516,213 B1 * | 2/2003 | Nevo ................................ 600/424 |
| 6,527,938 B2 * | 3/2003 | Bales et al. ...................... 205/229 |
| 6,699,186 B1 | 3/2004 | Wolinsky et al. |
| 6,729,336 B2 | 5/2004 | Da Silva et al. |
| 6,743,173 B2 * | 6/2004 | Penner et al. .................... 600/309 |
| 6,765,144 B1 * | 7/2004 | Wang et al. ....................... 174/36 |
| 6,901,296 B1 * | 5/2005 | Whitehurst et al. ............ 607/50 |
| 6,926,670 B2 * | 8/2005 | Rich et al. ....................... 600/459 |
| 7,218,210 B2 * | 5/2007 | Schoenberger et al. ....... 340/445 |
| 7,235,098 B2 * | 6/2007 | Palmaz ........................ 623/1.15 |
| 7,295,877 B2 * | 11/2007 | Govari ............................. 607/60 |
| 7,329,279 B2 * | 2/2008 | Haug et al. .................... 623/2.11 |
| 7,481,771 B2 * | 1/2009 | Fonseca et al. ............... 600/486 |
| 7,491,234 B2 * | 2/2009 | Palasis et al. ................. 623/1.42 |
| 2002/0040233 A1 * | 4/2002 | George et al. ...................... 607/2 |
| 2002/0188323 A1 * | 12/2002 | Penner et al. ..................... 607/2 |
| 2003/0229392 A1 * | 12/2003 | Wong ........................... 623/1.42 |
| 2004/0082866 A1 * | 4/2004 | Mott et al. ..................... 600/486 |
| 2004/0122494 A1 * | 6/2004 | Eggers et al. ................. 607/103 |
| 2004/0158310 A1 * | 8/2004 | Weber et al. .................. 623/1.15 |
| 2004/0176672 A1 | 9/2004 | Silver et al. |
| 2004/0225213 A1 * | 11/2004 | Wang et al. .................... 600/421 |

(Continued)

*Primary Examiner* — David Isabella
*Assistant Examiner* — Jonathan R Stroud
(74) *Attorney, Agent, or Firm* — Brooks, Cameron & Huebsch, PLLC

(57) ABSTRACT

Embodiments of the present invention relate to medical devices that provide signals to diagnostic equipment such that functionality of an implantable member can be determined. In particular, various designs and structures are utilized to signal tissue growth on an implantable member such as a stent. The tissue growth can limit flow through the stented lumen. If the growth has a thickness above a certain limit, a signal can be detected by diagnostic equipment such that a proper diagnosis can be made.

21 Claims, 9 Drawing Sheets

U.S. PATENT DOCUMENTS

| | | | |
|---|---|---|---|
| 2004/0230290 A1* | 11/2004 | Weber et al. | 623/1.15 |
| 2005/0043894 A1* | 2/2005 | Fernandez | 702/19 |
| 2005/0079132 A1* | 4/2005 | Wang et al. | 424/1.11 |
| 2005/0177223 A1* | 8/2005 | Palmaz | 623/1.15 |
| 2005/0209680 A1* | 9/2005 | Gale et al. | 623/1.15 |
| 2005/0283229 A1* | 12/2005 | Dugan et al. | 623/1.38 |
| 2006/0074479 A1* | 4/2006 | Bailey et al. | 623/1.13 |
| 2006/0280770 A1* | 12/2006 | Hossainy et al. | 424/423 |
| 2007/0027532 A1* | 2/2007 | Wang et al. | 623/1.44 |
| 2007/0055364 A1* | 3/2007 | Hossainy et al. | 623/1.38 |
| 2007/0112344 A1* | 5/2007 | Keilman | 606/41 |
| 2007/0123975 A1* | 5/2007 | Weber et al. | 623/1.16 |
| 2007/0156231 A1* | 7/2007 | Weber | 623/1.38 |
| 2007/0191816 A1* | 8/2007 | Behan et al. | 604/890.1 |
| 2007/0219623 A1* | 9/2007 | Palmaz | 623/1.15 |
| 2007/0299511 A1* | 12/2007 | Gale | 623/1.46 |
| 2008/0246368 A1* | 10/2008 | Auciello et al. | 310/321 |
| 2009/0062900 A1* | 3/2009 | Lal et al. | 623/1.15 |

* cited by examiner t=first time period

IMPLANTATION t=second time period t=third time period

MEDICAL DEVICE THAT SIGNALS LUMEN LOSS

BACKGROUND OF THE INVENTION

The present invention relates generally to devices for use in vascular treatments. More particularly, the present invention relates to devices used in vascular treatments that provide signals to diagnostic equipment.

Vascular stents are known medical devices used in various vascular treatments of patients. Stents commonly include a tubular member that is moveable from a collapsed, low profile, delivery configuration to an expanded, deployed configuration. In the expanded configuration, an outer periphery of the stent frictionally engages an inner periphery of a lumen. The deployed stent then maintains the lumen such that it is substantially unoccluded and flow therethrough is substantially unrestricted.

Some percentage of stents that are implanted suffer from luminal loss due to thrombosis, encrustation, or neointimal hyperplasia restenosis. If the patient develops symptoms associated with these situations, diagnostic procedures will be used to determine if the stented lumen is adequately functional, if another disease condition has presented itself, or if the stented lumen has become inadequately functional. The diagnostic procedures may include initial non-invasive techniques such as radiography, magnetic resonance imaging (MRI), computed tomography (CT) and/or measurement of chemistry, temperature, pressure and other parameters. Additionally, the diagnosis may include minimally invasive procedures such as angiography. However, angiography procedures can disrupt a patient's recovery and can be uncomfortable and painful to endure. Even so, the diagnostic procedures may be inaccurate, imprecise, and inconclusive as to determining the accurate functionally of the implanted stent.

SUMMARY OF THE INVENTION

Embodiments of the present invention relate to medical devices that provide signals to diagnostic equipment such that functionality of an implantable member can be determined. In particular, various designs and structures are utilized to signal tissue growth on an implantable member such as a stent. The tissue growth can limit flow through the stented lumen. If the growth has a thickness above a certain limit, a signal can be detected by diagnostic equipment such that a proper diagnosis can be made.

DETAILED DESCRIPTION OF ILLUSTRATIVE EMBODIMENTS

Figure 1:
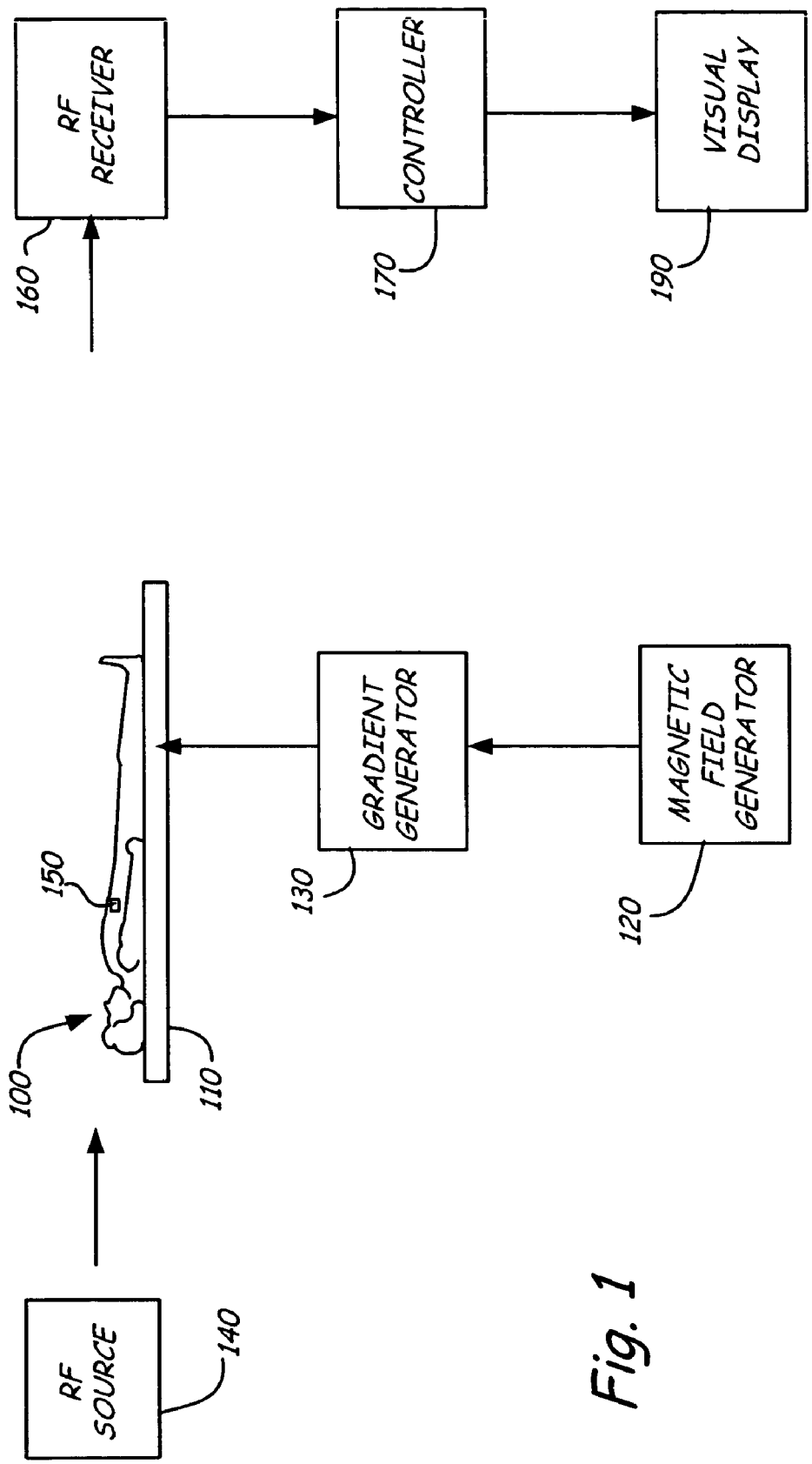
FIG. 1 is a partial block diagram of an illustrative magnetic resonance imaging system.

One particular diagnostic system that can be used with the present invention is a magnetic resonance imaging (MRI) system. FIG. 1 is a partial block diagram of an illustrative MRI system. In FIG. 1, subject 100 on support table 110 is placed in a homogeneous magnetic field generated by magnetic field generator 120. Magnetic field generator 120 typically comprises a cylindrical magnet adapted to receive subject 100. Magnetic field gradient generator 130 creates magnetic field gradients of predetermined strength in three mutually orthogonal directions at predetermined times. Magnetic field gradient generator 130 is illustratively comprised of a set of cylindrical coils concentrically positioned within magnetic field generator 120. A region of subject 100 into which a device 150, shown as a stent, has been inserted, is located in the body of subject 100.

RF source 140 radiates pulsed radio frequency energy into subject 100 and stent 150 at predetermined times and with sufficient power at a predetermined frequency to influence nuclear magnetic spins in a fashion known to those skilled in the art. The influence on the atoms causes them to resonate at the Larmor frequency. The Larmor frequency for each spin is directly proportional to the absolute value of the magnetic field experienced by the atom. This field strength is the sum of the static magnetic field generated by magnetic field generator 120 and the local field generated by magnetic field gradient generator 130. In an illustrative embodiment, RF source 140 is a cylindrical external coil that surrounds the region of interest of subject 100. Such an external coil can have a diameter sufficient to encompass the entire subject 100. Other geometries, such as smaller cylinders specifically designed for imaging the head or an extremity can be used instead. Non-cylindrical external coils such as surface coils may alternatively be used.

External RF receiver 160 illustratively detects RF signals emitted by the subject in response to the radio frequency field created by RF source 140. In an illustrative embodiment, external RF receiver 160 is a cylindrical external coil that surrounds the region of interest of subject 100. Such an external coil can have a diameter sufficient to encompass the entire subject 100. Other geometries, such as smaller cylinders specifically designed for imaging the head or an extremity can be used instead. Non-cylindrical external coils, such as surface coils, may alternatively be used. External RF receiver 160 can share some or all of its structure with RF source 140 or can have a structure entirely independent of RF source 140. The region of sensitivity of RF receiver 160 is larger than that of the stent 150 and can encompass the entire subject 100 or a specific region of subject 100. The RF signals detected by external RF receiver 160 are sent to imaging and tracking controller unit 170 where they are analyzed. Controller 170 displays signals received by RF receiver 160 on visual display 190.

Establishing a homogenous, or uniform, magnetic field with magnetic field generator 120 in addition to switched linear gradient magnetic fields activated in various sequences as well as timely switching the RF radiowave in various sequences, as known in the art, enables the production of internal images of subject 100. It is common for the material and structure of stent 150 to affect the magnetic field around stent 150 during an MRI procedure. One effect that can be detected by an MRI system is associated with Faraday's Law. Faraday's Law simply states that any change in a magnetic environment of a conductive coil will cause a voltage (emf) to be "induced" in the coil. Stent 150 or portions thereof can act as a coil when implanted in a subject during an MRI process. The MRI system can be calibrated to detect this electric voltage. According to Faraday's Law, the induced emf in a coil is equal to the negative of the rate of change of magnetic flux through the coil times the number of turns in the coil. When an emf is generated by a change in magnetic flux, the polarity of the induced emf produces a current creating a magnetic field that opposes the change which produces it. Accordingly, the induced magnetic field inside any loop of wire acts to keep the magnetic flux inside the loop constant.

Figure 2:
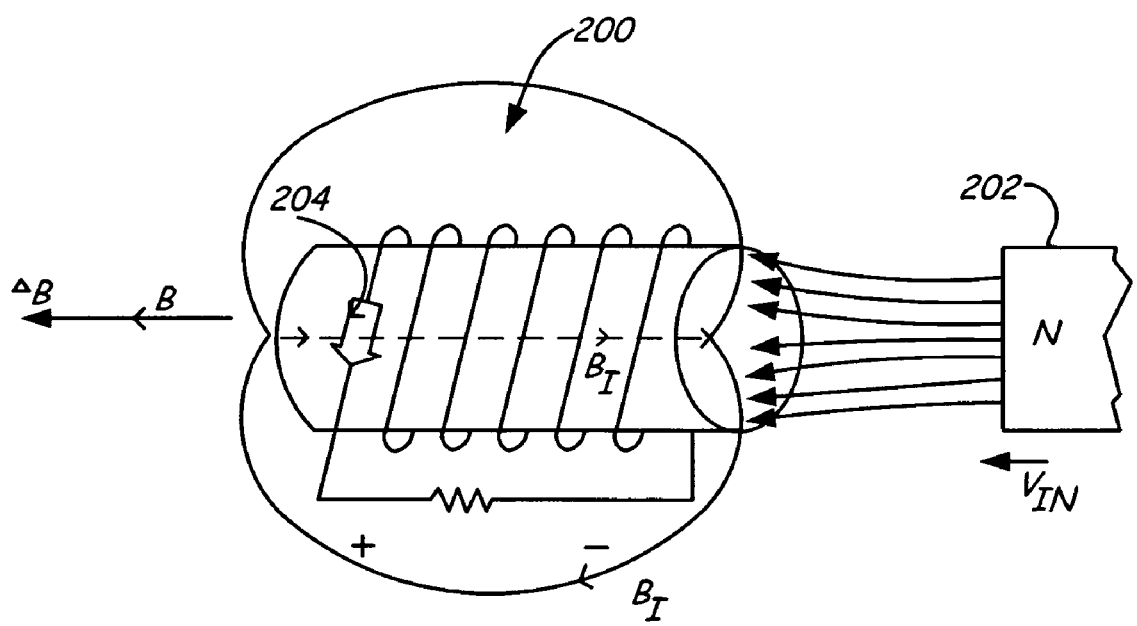
FIG. 2 is an illustration of a coil in a changing magnetic field.

FIG. 2 further illustrates this effect. Coil 200 has been placed in a magnetic field produced by magnet 202. The magnetic field is represented by a vector B. Any change in magnetic field B, herein represented as ΔB, causes a current, represented as arrow 204, to be produced in coil 200. Current 204 causes a magnetic field $B_I$ to be induced, which opposes the change ΔB.

During various phases of an MRI process to influence the nuclear spins, a change in the magnetic field inside the stent is generated. For example, gradient generator 130 may generate a pulse in order to influence spins to be analyzed by controller 170. The gradient generator 130 thus changes the magnetic field and accordingly a change in magnetic field proximate the stent is opposed by Faraday's Law.

Figure 3:
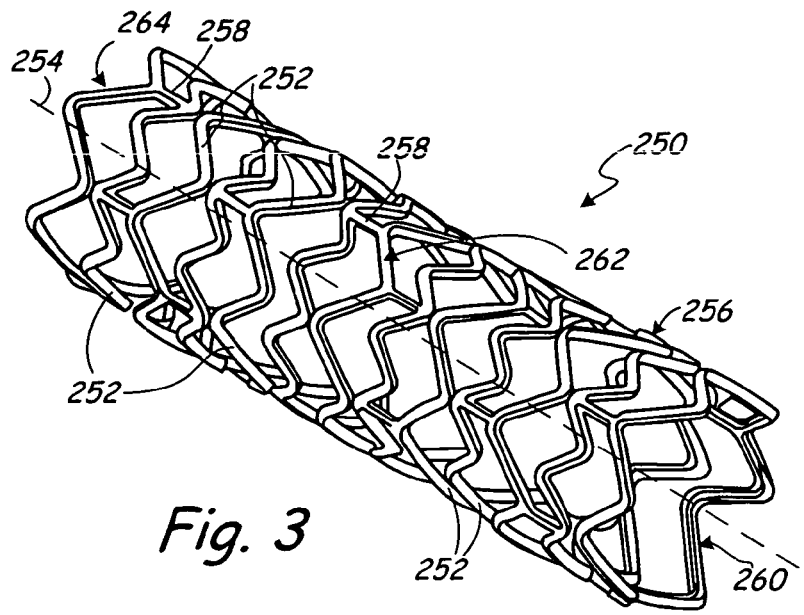
FIG. 3 is a perspective view of a stent.

FIG. 3 illustrates an exemplary stent 250. Stent 250 includes a plurality of rings (sometimes referred to as struts, bands or cells) 252 wrapped around a central axis 254 to form a generally tubular structure 256. Rings 252 are connected by a plurality of connectors (sometimes referred to as bridges or links) 258. Illustratively, rings 252 are equally spaced about axis 254 and flexible to allow bending of tubular structure 256. The flexibility of tubular structure 256 allows stent 250 to be placed in various lumens of different shapes and sizes. Rings 252 frictionally engage an inner periphery of a lumen when tubular structure 256 is open to allow fluid flow therethrough. Stent 250 further includes signaling members 260, 262, and 264 that signal tissue growth around stent 250. Signaling members 260, 262 and 264 are used in order to utilize the effect of Faraday's Law on the stent. Various stent designs are discussed below in accordance with embodiments of the present invention.

It is known that stent 250 can become clogged with thrombus or tissue in-growth, causing occlusion of flow through stent 250. The tissue of the lumen can be injured by the act of implanting the stent. The response of the body is to heal the injury. During healing, tissue can form on the stent from thrombus deposition or cellular seeding and proliferate thickening. Additionally, tissue inflammation can be a part of the healing response. This tissue occlusion prevents stent 250 from operating adequately.

In one embodiment of the present invention, at least one electrically conductive pathway having a switch in an open position is provided on the stent 250. When stent lumen occlusion occurs, inflammation from the tissue covering the switch can move the switch to the closed position. As a result, closed conductive loops occur within the stent. The magnetic fields resulting from the conductive pathways interact with the magnetic fields from the MRI system and the resulting diagnostic image is changed. This event signals stent lumen loss.

In the embodiment illustrated, signaling members 260, 262 and 264 each include a closed-loop electrical pathway with switches. In particular, signaling members 260 and 264 are used at each end of the stent and signaling member 262 is used in the middle of the stent length. Signaling members 260 and 264 at the end of the stent signal stent-end occlusion and signaling member 262 at mid-length signal in-stent occlusion. If it is desired to signal stent occlusion at more locations along the stent length, additional signaling members can be used.

In embodiments of the present invention, rings 252 and connectors 258 of stent 250 can be made of nonconductive and nonmagnetic (diamagnetic) materials that do not interact with an MR image, such as biostable or bioabsorbable polymers. The electrical pathway of signaling members 260, 262 and 264 can be made using similar technology for making printed circuit boards. The electronically conductive pathway could be applied to the inner diameter (ID) surface of the stent 250 by pressure-transfer and adhesion of a metal preform or by masking the ID surface of the stent (except for the surface area intended for the pathway) and depositing a conductive metal by electroplating, dip-coating, metal vapor deposition, and de-masking the stent. Another method of applying the pathway is by laser deposition. For example, Potomac (www.potomac-laser.com) can deposit metal features as small as 2 microns. Additionally, the pathway can be made of a biocompatible conductive metal with low magnetic susceptibility such as platinum, gold, niobium, titanium, tantalum, niobium, titanium, tantalum, niobium, silver or chromium. The stent substrate could be made as a tube with the strut pattern cut in to the material by abrasive water-jet, mechanical machining, chemical machining, laser machining, die-cutting, or plastic injection molding. Another approach for stent fabrication is that the stent ring and connector pattern could be cut into flat plastic strip stock followed by rolling and bonding a strip into a tubular stent configuration.

Figure 4:
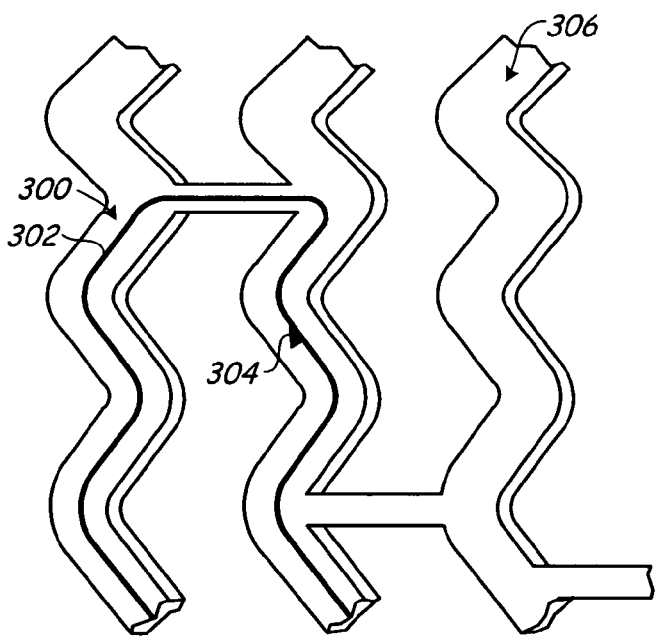
FIG. 4 is a top view of a portion of a signaling member.
Figure 5:
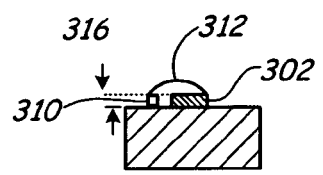
FIG. 5 is a sectional view of a switch.

FIGS. 4 and 5 illustrate an exemplary embodiment of including a switch as a signaling member in stent 250 of FIG. 3. FIG. 4 is a schematic view of a portion of a signaling member 300 and FIG. 5 is a sectional view of a portion of the signaling member 300. Signaling member 300 includes a conductive pathway 302 and a switch 304. Signaling member 300 is positioned on an inner diameter surface 306 of a stent. In this embodiment, the stent is made of non-conductive and non-magnetic materials.

Figure 6A:
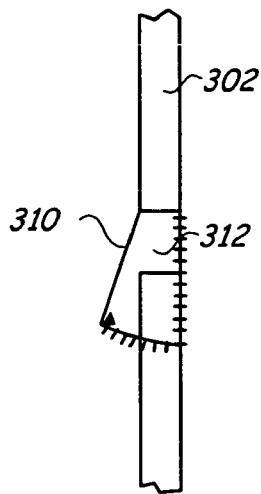
FIG. 6A is a schematic view of a switch in an open position.
Figure 6B:
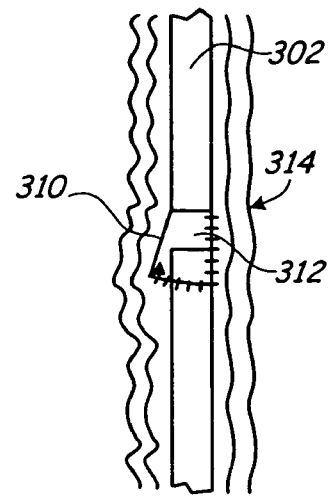
FIG. 6B is a schematic view of the switch of FIG. 6A in a closed position.

FIG. 6A illustrates an open position of switch 304 while FIG. 6B illustrates a closed position of switch 304. Switch 304 includes a switch arm 310 and a cover 312. Cover 312 can be an isolation film such as polyethylene, ePTFE, or SIBS to prevent disturbance of operation of switch arm 310. As tissue (schematically illustrated at 314) builds up around switch arm 310 and exerts pressure on switch arm 310 from inflammation and growth, the switch arm 310 is pushed toward pathway 302. When contact between pathway 302 and switch arm 310 is made, as shown in FIG. 6B, pathway 302 is closed and conductive. An MRI system can be calibrated to detect the conductivity of pathway 302.

Switch arm 310 can be made to have a sharp point on it for making contact with the pathway 302. The point can scratch or indent the pathway surface to aid in making a strong electrical connection. The surface area through which switch arm 310 travels to contact the pathway 302 is covered by cover 312 so as to prevent thrombus and/or tissue formation that could inhibit travel of switch arm 310.

A height 316 of the switch arm can be made to be equal to a selected limit of tissue thickness on the stent ID surface 306 that is allowed during restenosis. Minimal and acceptable tissue thickness less than the switch arm height would not cause switch arm 310 to travel to pathway 302. Large and unacceptable tissue above the selected limit would cause switch arm 310 to move to contact with pathway 302.

The switch 304 can also be designed so that it has a certain amount of spring force that must be applied to close it. This spring force can be matched to a certain amount of tissue thickness or lumen loss; e.g. 30% lumen loss or tissue thickness of two times the thickness of the stent. This force can be modeled and predicted with finite element analysis using arterial or vessel pressure and the thickness and compressive strength of the occlusive material; e.g. atherosclerotic plaque, tumor, endothelium, or smooth muscle cells.

Figure 7A:
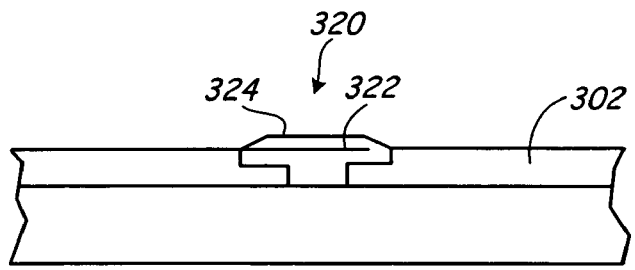
FIG. 7A is a schematic view of a switch in an open position.
Figure 7B:
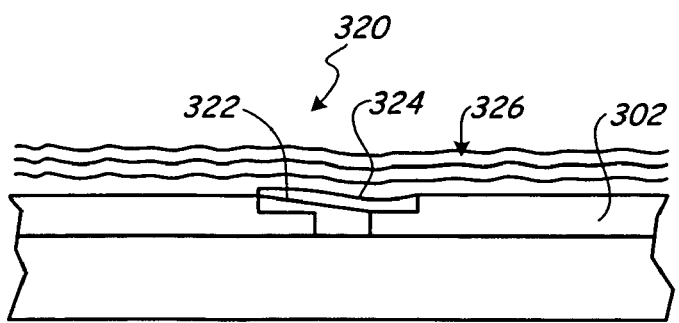
FIG. 7B is a schematic view of the switch of FIG. 7A in a closed position.

Alternative switch designs can also be used in place of switch 304. FIGS. 7A and 7B illustrate a schematic view of an alternative switch 320 that is coupled to pathway 302. FIG. 7A shows an open position of switch 320, which includes switch arm 322 and cover 324. In this embodiment, a "top-switch" design is used. Switch arm 322 is forced down by tissue growth on top of the stent surface. FIG. 7B shows a closed position of switch 320, where tissue 326 has forced switch arm 322 into contact with pathway 302.

Figure 8A:
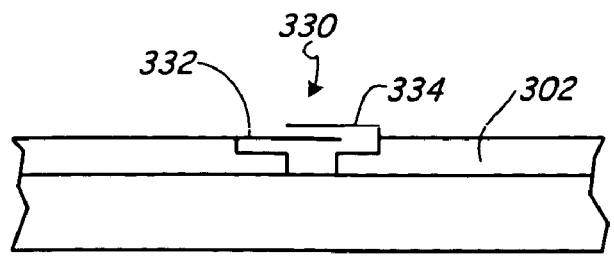
FIG. 8A is a schematic view of a switch in an open position.
Figure 8B:
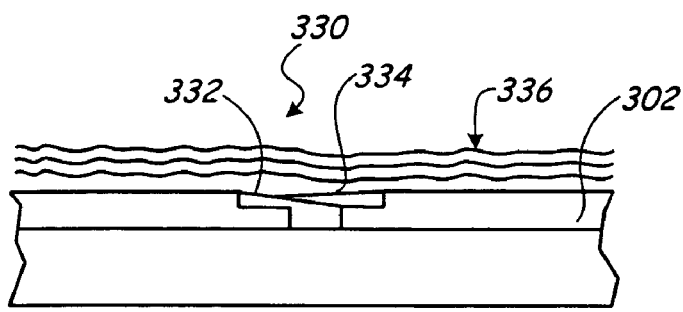
FIG. 8B is a schematic view of the switch of FIG. 8A in a closed position.

FIGS. 8A and 8B are schematic illustrations for a top-switch design without a cover. In this embodiment, switch 330 includes two overlapping, but initially non-contacting, switch arms 332 and 334. As pressure is applied to the switch arms 332, 334 by tissue 336, the arms 332 and 334 bend down and make contact with each other to close the circuit of pathway 302.

Figure 9A:
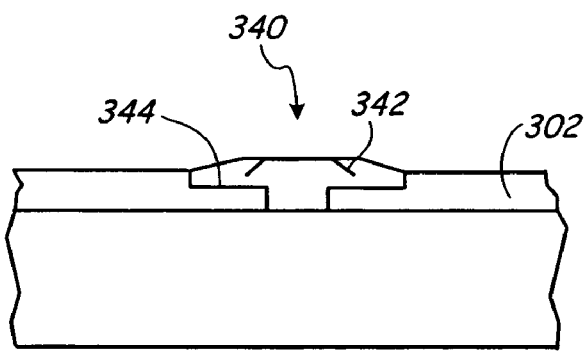
FIG. 9A is a schematic view of a switch in an open position.
Figure 9B:
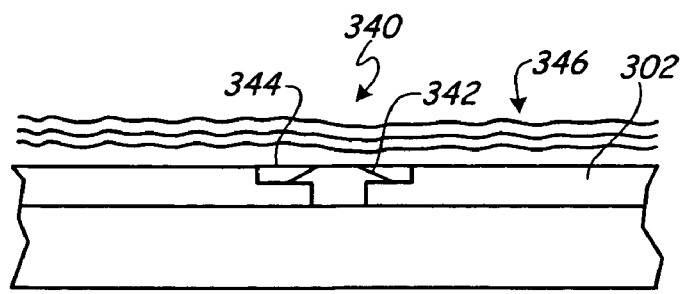
FIG. 9B is a schematic view of the switch of FIG. 9A in a closed position.

FIGS. 9A and 9B illustrate another embodiment of a top-switch design. Switch 340 includes a conductive bridge element 342 that initially is raised above a gap between segments of pathway 302 and protected by a cover 342. As pressure is applied to the cover 342 by tissue 346, the bridge 342 moves down and electrical continuity is established when bridge 342 contacts the pathway segments.

Figure 10:
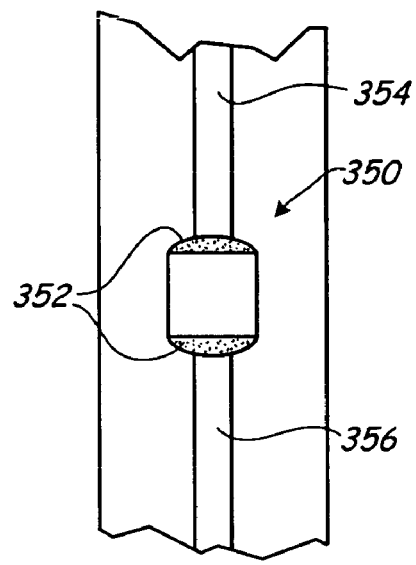
FIG. 10 is a schematic top view of a switch.
Figure 11A:
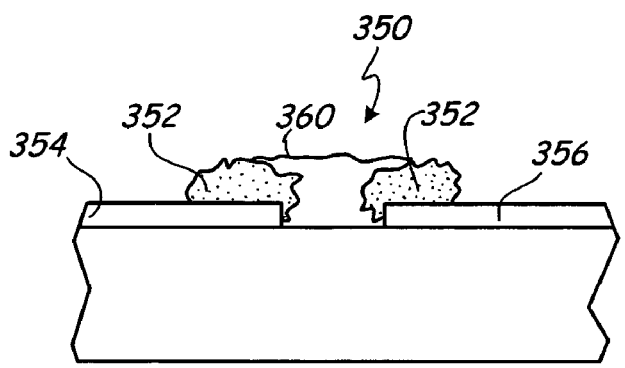
FIG. 11A is a schematic view of the switch of FIG. 10 in an open position.
Figure 11B:
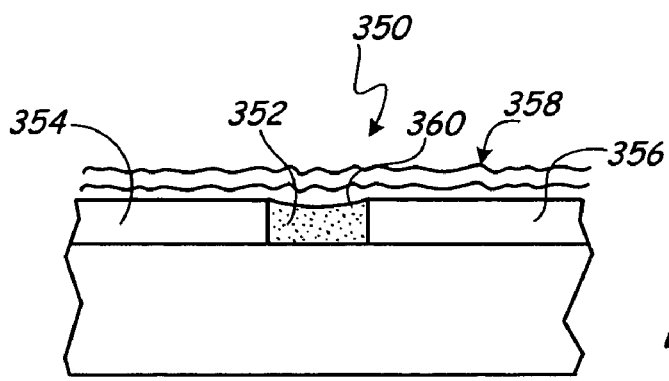
FIG. 11B is a schematic view of the switch of FIG. 10 in a closed position.

FIG. 10 illustrates another example of a pathway switch. Switch 350 includes a conductive, flowable filler material 352 on each side of a gap between pathway segment ends 354 and 356. FIGS. 11A and 11B illustrate an open position and a closed position of switch 350, respectively. As tissue 358 grows on the stent surface, the filler material 352 is pushed into the gap between ends 354 and 356. When the filler material 352 bridges the gap, the circuit is closed. The gap between the segment ends 354 and 356, as well as the filler material 352, is covered by an isolation film material 360. The filler material 352 could be a gel that is loaded with 10-50 volume percent of a radiopaque agent such as less than 2 micron tantalum powder metal particles, for example. The gel could be solid at room temperature and flowable at body temperature.

Figure 12:
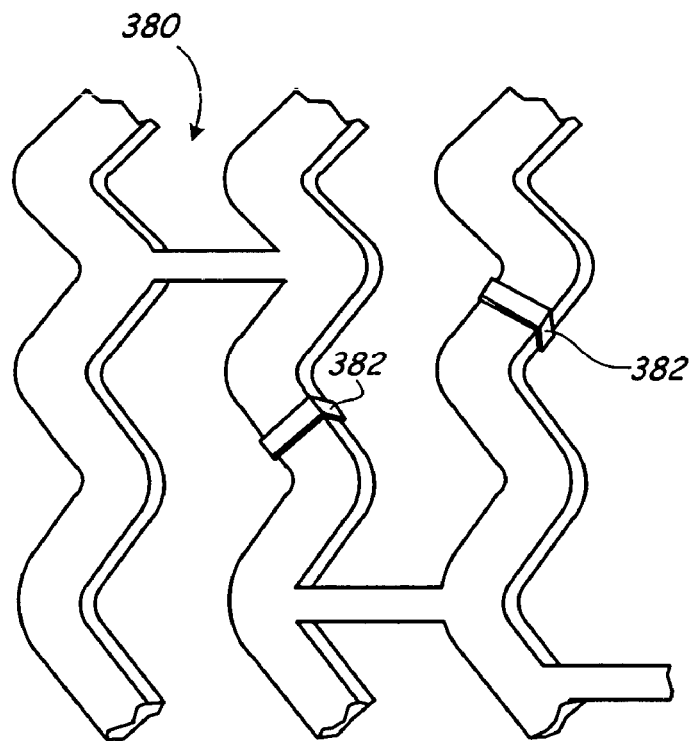
FIG. 12 is a top view of a portion of a signaling member.
Figure 13A:
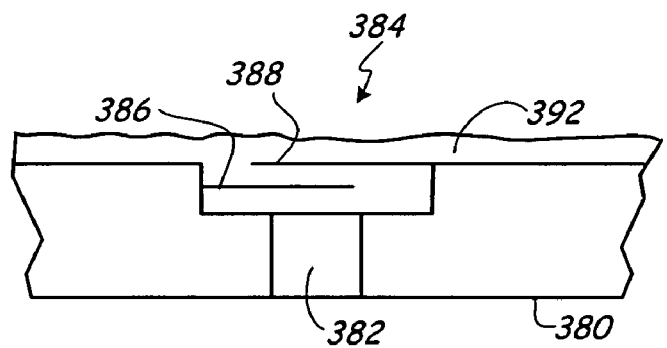
FIG. 13A is a schematic view of a switch in an open position.
Figure 13B:
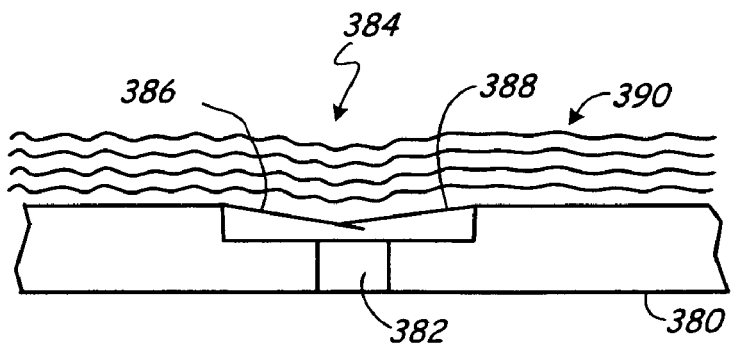
FIG. 13B is a schematic view of the switch of FIG. 13A in a closed position.

FIG. 12 illustrates an alternative embodiment that utilizes a metal stent design to signal tissue growth. Metal stent 380 includes non-conductive spacers 382. The non-conductive spacers 382 prevent conductive loops from forming in stent 380. Exemplary embodiments of metal stents with non-conductive spacers are further described in Weber et al., U.S. patent application Ser. No. 10/636,063, filed on Aug. 7, 2003. One or more of the non-conductive spacers 382 can include a switch 384 in an open position, as shown in FIG. 13A. Switch 384 includes conductive switch arms 386 and 388 on stent 380 above spacer 382. FIG. 13B illustrates switch 384 in a closed position, wherein tissue 390 has forced switch arms 386 and 388 together. FIG. 13A also illustrates a coating 392 provided on stent 380. This coating 392 can include a drug-eluting material or another material as desired. The stent 380 can be made out of biocompatible metals with low magnetic susceptibility such as niobium, titanium, platinum or tantalum.

Figure 14:
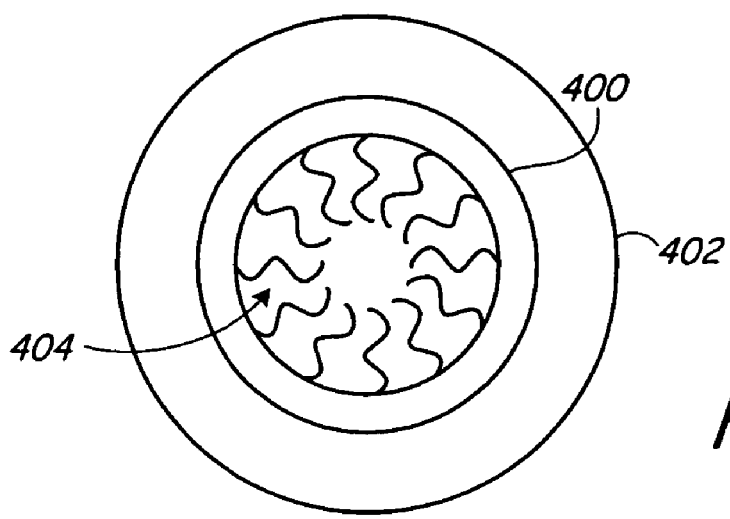
FIG. 14 is a sectional view of a stent in a lumen.

FIG. 14 is a schematic of a cross-section of a stented vessel in accordance with an alternative embodiment of the present invention. Stent 400 has been placed in lumen 402 and includes a signaling number 404. Signaling number 404 includes a plurality of electrically conductive structural members such as loops, coils and/or other structures that dangle in the stent. In one embodiment, stent 400 can be made of a non-conductive polymer material. The material of the structural members of signaling member 404 is non-thrombogenic and resists bacteria adhesion and mucosal and bile sludge attachment. The design and material selection of the members is made such that it does not promote stent obstruction. There is also a characteristic electrical conductivity between the structure components in the presence of flowing vessel contents. As cellular tissue or viscous matter builds up between the structural members, the electrical conductivity between them changes. This change results in a more conductive path through the tissue between the structural members. This situation can be recognized by MRI equipment that is tuned (calibrated) to recognize such conditions. The structural members of signaling member 404 can include high MRI compatibility materials; e.g. titanium, niobium, and tantalum.

Figure 15:
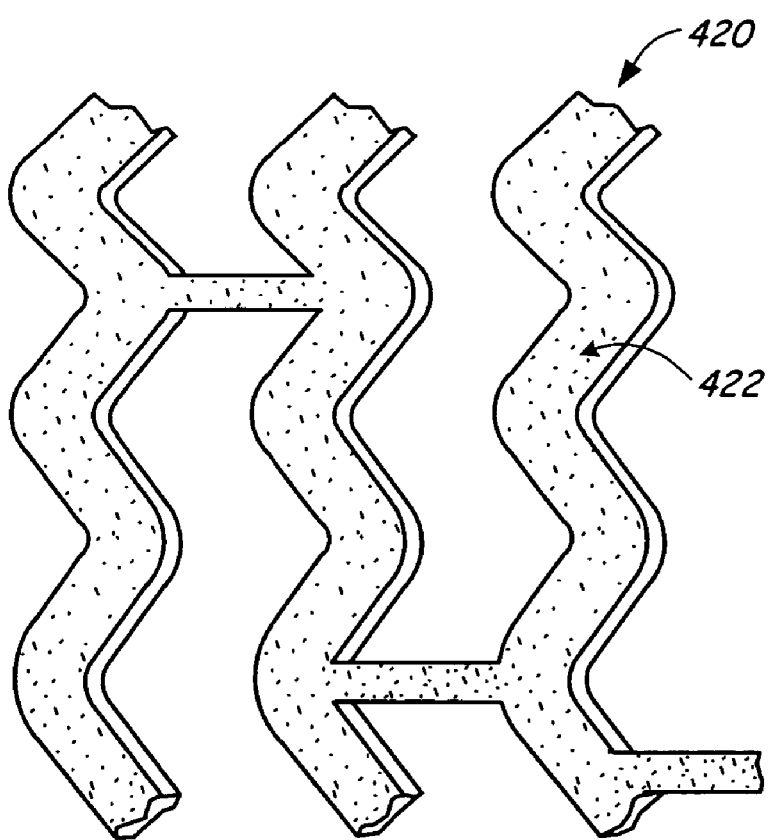
FIG. 15 is a top view of a portion of a stent having a pressure sensitive coating.

FIG. 15 illustrates another embodiment of the present invention, wherein a pressure sensitive coating is positioned on a stent ID surface. Stent 420 includes a coating 422. The coating 422 could be a nanostructure of a honeycomb design wherein a piezoelectric current is created if a layer of coating 422 is deformed. When biological material such as tissue is deposited on the stent ID and thus reduces the lumen diameter, hydrostatic pressure at this location would increase since the vessel contents would be forced into a smaller opening. Increased pressure on the stented lumen wall deforms the nanostructure of the coating 422 and cause a piezoelectric effect. This effect can be detected in a MRI exam with equipment that was tuned (calibrated) to a characteristic signal.

Other diagnostic systems that can be used with the present invention include x-ray systems, computed topography systems and blood analysis systems. When using these systems, an elutable coating is placed on a stent. For example, a drug-eluting coating of a stent can include a harmless dose of an elutable radiopaque substance. The substance can be designed with a specified release rate from the stent coating and a diffusion rate through cellular tissue that would form on the stent ID surface during thrombosis, encrustation, or neointimal hyperplasia restenosis. The substance is designed to elute slowly from the stent and harmlessly migrate away from the stent by the flushing action of the vessel contents. A baseline radiograph or CT scan can be made of the stent just after implantation to record an image of the stent and determine the radiopacity of the stent with the coating. The overall radiopacity of the stent would change over time, becoming less and less as the radiopaque substance is released and migrates away from the stent. If the stent lumen became obstructed, the release and flushing away of the radiopaque substance is inhibited and slowed. The substance would migrate from the stent coating into the obstructive material and the stent would appear to have a thicker wall. Thus, the radiopacity level would not change at the same rate as an unobstructed stent in corresponding x-ray and CT images.

The signaling of stented lumen loss can also be performed by a chemical that is released from other coatings on a stent into systemic circulation. Exemplary chemicals would be easily detected and quantified in a standard blood test or other easy medical chemical analysis. For example, a drug-eluting coating could have a component chemical that is designed to release over a period of time in which the stent is desired to be effective. This chemical would have a short life in systemic circulation and be broken down to harmless by-products relatively quickly. A blood test could be used to quantify the amount of chemical that is present at any moment in time. The amount is an indication of the current release of the chemical from the stent. The chemical would be designed such that it could elute from the stent, but could not migrate through and release from a significant build-up of obstructive material that would form within a stented lumen. A molecule designed to bind to obstructive tissue, be decomposed by obstructive tissue, or to be too large to diffuse through thick tissue at a fast rate can be used. If the patient became symptomatic of a possible stent obstruction, a blood test could be performed to measure for the presence of the chemical. The amount of the chemical detected would be compared to data for conditions of different amounts of stent obstruction to provide information as to whether or not the lumen was likely obstructed.

Figure 16:
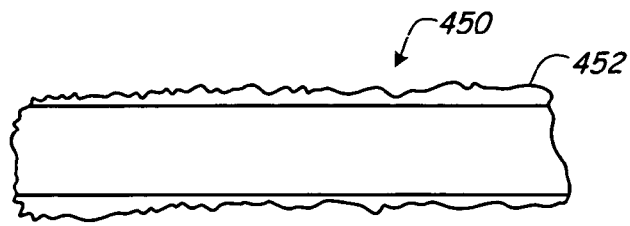
FIG. 16 is a schematic view of a stent having an elutable coating.

FIG. 16 is a schematic view of a portion of a stent having an elutable coating that can be used to signal stent occlusion as discussed above. Stent 450 includes a coating 452 that includes an elutable agent detectable on one or more diagnostic systems and/or procedures. When there is only limited tissue growth over the ID surface of stent 450, the elutable agent diffuses out of coating 452 over time and is flushed away. However, if there is tissue growth to a significant thickness, the diffusion of the agent is slowed.

Figure 17:
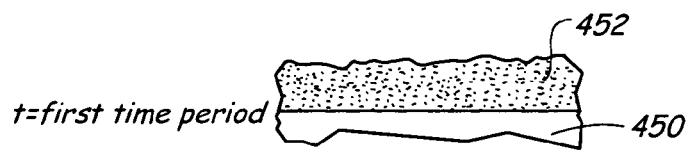
FIG. 17 is a schematic close-up view of the elutable coating of the stent of FIG. 16 at a first time period.
Figure 18A:
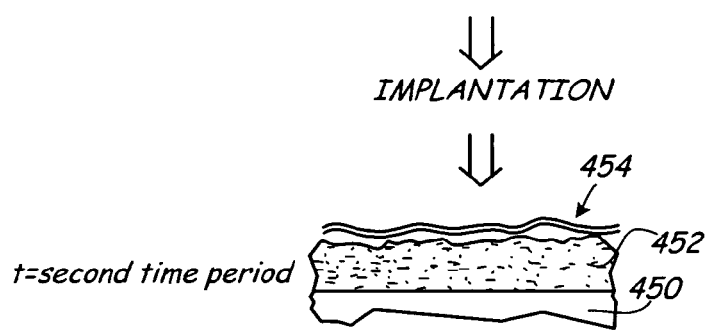
FIG. 18A is a schematic view of the elutable coating of the stent of FIG. 16 at a second time period with limited tissue growth on the stent.
Figure 18B:
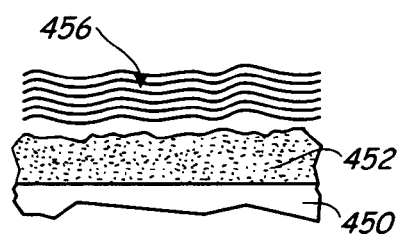
FIG. 18B is a schematic view of the elutable coating of the stent of FIG. 16 at a second time period with extensive tissue growth on the stent.
Figure 19A:
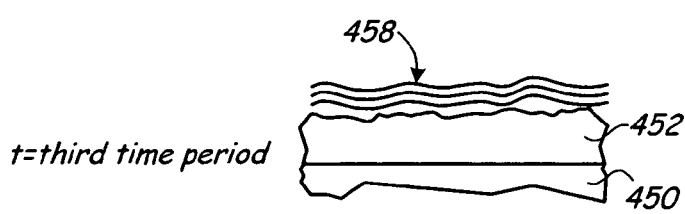
FIG. 19A is a schematic view of the elutable coating of the stent of FIG. 16 at a third time period with limited tissue growth on the stent.
Figure 19B:
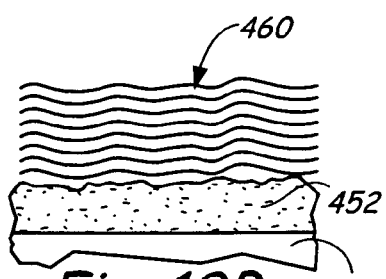
FIG. 19B is a schematic view of the elutable coating of the stent of FIG. 16 at a third time period with extensive tissue growth on the stent.

FIG. 17 schematically illustrates the agent in coating 452 at a first time period, normally when stent 450 is placed in a lumen. FIGS. 18A and 18B schematically illustrate the levels of the agent at a second time period with limited tissue growth and extensive tissue growth, respectively. For example, the second time period could be about 4 weeks after placement of stent 450. In FIG. 18A, a relatively limited amount of tissue (schematically illustrated at 454) has grown on stent 450, and normal levels of the agent within coating 452 have been released into the patient's body. In contrast, FIG. 18B includes relatively extensive tissue growth (schematically illustrated at 456), and thus low levels of the agent within coating 452 have been released into the patient's body. In the occlusive scenario of FIG. 18B, the stent ID will retain the agent than it should if there had not been significant restenosis. FIGS. 19A and 19B schematically illustrate the levels of the agent at a third time period with limited tissue growth and extensive tissue growth, respectively. In FIG. 19A, limited tissue growth 458 has allowed the agent in coating 452 to be completely flushed into the patient's system. In contrast, FIG. 19B shows extensive tissue growth 460, which has prevented the agent within coating 452 to be released into the patient's system.

In a further embodiment, an elutable radiopaque agent be incorporated into a stent coating that is much thicker than the drug-eluting coating. This increased thickness would allow the radiopacity of the agent to be more readily resolved in radiographic images than when the agent is contained within a thin drug eluting stent coating. For example, the drug-eluting coating might be on the order of less than 0.0001" thick while the stent drug eluting coating containing the elutable radiopaque agent might be 0.0005-0.0020" thick. Alternatively, the elutable radiopaque agent could be included within a polymer resin of a bioabsorbable polymer stent so that a coating would not be needed. Alternately, instead of using a radiopaque agent, the polymer stent or stent coating could be loaded with a chemical species that would be detected in a standard blood assay test.

Although the present invention has been described with reference to illustrative embodiments, workers skilled in the art will recognize that changes may be made in form and detail without departing from the spirit and scope of the invention.

What is claimed is:

1. A stent, comprising:
    a structural element; and
    a signaling member coupled to the structural element to signal a level of tissue growth on the structural element, where the signaling member includes a conductive pathway having a switch including a flowable filler material, where the switch closes in response to the level of tissue growth to provide a closed loop electrical pathway on the structural element and the switch includes a cover extending from an outer edge of the conductive pathway to an outer edge of the switch defining an area completely enclosed by the cover where the flowable filler material travels through a portion of the area completely enclosed by the cover to contact the conductive pathway forming the closed loop electrical pathway, where the cover prevents any tissue formation in the area completely enclosed by the cover.

2. The stent of claim 1, wherein the cover prevents any tissue formation that inhibits travel of the switch.

3. The stent of claim 1 wherein the flowable filler material is conductive and closes the conductive pathway in response to the level of tissue growth on the structural element.

4. The stent of claim 1 wherein the structural element comprises a generally tubular structure.

5. The stent of claim 4 wherein the generally tubular structure includes electrically conductive structural members spaced apart by nonconductive spacers and wherein the signaling member includes a switch that is adapted to electrically couple the electrically conductive structural members in response to the level of tissue growth.

6. The stent of claim 4, wherein the signaling member comprises a plurality of electrically conductive members extending from an inside surface of the tubular structure.

7. The stent of claim 1 wherein the signaling member includes at least one of platinum, iridium, tantalum, titanium, niobium, hafnium and gold.

8. The stent of claim 1 wherein the signaling member includes a pressure sensitive coating having a piezoelectric material.

9. The stent of claim 1 wherein the signaling member includes an elutable material.

10. The stent of claim 9 wherein the elutable material is a radiopaque coating.

11. The stent of claim 9 wherein the elutable material is a chemical that is detectable in a blood test.

12. The stent of claim 9 wherein the elutable material forms part of the structural element.

13. A stent, comprising:
a generally tubular structure, where the generally tubular structure includes a conductive pathway having a switch including a flowable filler material, where the switch closes in response to a level of tissue growth to provide a closed loop electrical pathway on the generally tubular structure, and a cover extending from an outer edge of the conductive pathway to an outer edge of the switch to define an area completely enclosed by the cover such that the switch travels through a portion of the area completely enclosed by the cover to form the closed loop electrical pathway, where the cover prevents tissue formation in the area completely enclosed by the cover.

14. The stent of claim 13 wherein the generally tubular structure includes electrically conductive structural members spaced apart by nonconductive spacers and wherein the switch is adapted to electrically couple the electrically conductive structural members in response to the level of tissue growth.

15. The stent of claim 13 wherein the generally tubular structure includes at least one of platinum, iridium, tantalum, titanium, niobium, hafnium and gold.

16. The stent of claim 13, wherein the generally tubular structure includes a plurality of electrically conductive members extending from an inside surface of the tubular structure.

17. The stent of claim 13 wherein the generally tubular structure includes a pressure sensitive coating having a piezoelectric material.

18. The stent of claim 13 wherein the generally tubular structure includes an elutable material.

19. The stent of claim 18 wherein the elutable material is a radiopaque coating.

20. The stent of claim 18 wherein the elutable material is a chemical that is detectable in a blood test.

21. The stent of claim 18 wherein the elutable material forms part of the generally tubular structure.

* * * * *